US009051355B2

(12) United States Patent
Tamori et al.

(10) Patent No.: US 9,051,355 B2
(45) Date of Patent: Jun. 9, 2015

(54) FILLER FOR AFFINITY CHROMATOGRAPHY AND METHOD FOR ISOLATING IMMUNOGLOBULIN

(75) Inventors: Kouji Tamori, Minato-ku (JP); Tetsuo Fukuta, Minato-ku (JP); Masaaki Miyaji, Minato-ku (JP); Yong Wang, Minato-ku (JP); Takayoshi Abe, Minato-ku (JP); Yusuke Okano, Minato-ku (JP); Masaki Momiyama, Minato-ku (JP); Takahiro Kawai, Minato-ku (JP)

(73) Assignee: JSR CORPORATION, Tokyo (JP)

( * ) Notice: Subject to any disclaimer, the term of this patent is extended or adjusted under 35 U.S.C. 154(b) by 246 days.

(21) Appl. No.: 13/636,410

(22) PCT Filed: Mar. 23, 2011

(86) PCT No.: PCT/JP2011/056871
§ 371 (c)(1),
(2), (4) Date: Sep. 21, 2012

(87) PCT Pub. No.: WO2011/118599
PCT Pub. Date: Sep. 29, 2011

(65) Prior Publication Data
US 2013/0041135 A1    Feb. 14, 2013

(30) Foreign Application Priority Data
Mar. 24, 2010 (JP) ................................. 2010-068794

(51) Int. Cl.
*A61K 38/00*    (2006.01)
*C07K 1/22*    (2006.01)
*B01D 15/38*    (2006.01)
*B01J 20/286*    (2006.01)
*B01J 20/288*    (2006.01)
*B01J 20/32*    (2006.01)

(52) U.S. Cl.
CPC ............. *C07K 1/22* (2013.01); *B01D 15/3804* (2013.01); *B01J 20/286* (2013.01); *B01J 20/288* (2013.01); *B01J 20/3274* (2013.01); *C07K 2317/10* (2013.01); *B01J 20/3219* (2013.01)

(58) Field of Classification Search
None
See application file for complete search history.

(56) References Cited

U.S. PATENT DOCUMENTS

| 2008/0230478 | A1* | 9/2008 | Johansson et al. | ........... 210/656 |
| 2010/0105879 | A1 | 4/2010 | Katayose et al. | |
| 2010/0221844 | A1 | 9/2010 | Bian et al. | |
| 2010/0286373 | A1 | 11/2010 | Majima et al. | |
| 2011/0136169 | A1* | 6/2011 | Anderson et al. | ........... 435/69.1 |
| 2011/0262748 | A1 | 10/2011 | Tamori et al. | |

FOREIGN PATENT DOCUMENTS

| CN | 101298475 A | 11/2008 |
| CN | 101775069 A | 7/2010 |
| EP | 1 992 692 A1 | 11/2008 |
| EP | 2 128 616 A1 | 12/2009 |
| EP | 2 339 339 A1 | 6/2011 |
| JP | 6 281638 | 10/1994 |
| JP | 2006-304633 A | 11/2006 |
| WO | WO 2006/094467 A1 | 9/2006 |
| WO | WO 2010/035756 A1 | 4/2010 |
| WO | WO 2010/035757 A1 | 4/2010 |

OTHER PUBLICATIONS

Mitsuru Tashiro, et al., "Structures of bacterial immunoglobulin-binding domains and their complexes with immunoglobulins," Current Opinion in Structural Biology, vol. 5, No. 4, Aug. 31, 1995, pp. 471-481.
Graslund, S., et al., "Single-vector three-frame expression systems for affinity-tagged proteins," FEMS Microbiology Letters, vol. 215, No. 1, pp. 139 to 147, (2002).
Graslund, S., et al., "A novel affinity gene fusion system allowing protein A-based recovery of non-immunoglobulin gene products," Journal of Biotechnology, vol. 99, No. 1, pp. 41 to 50, (2002).
Mateo, C., et al., "One-Step Purification, Covalent Immobilization, and Additional Stabilization of Poly-His-Tagged Proteins Using Novel Heterofunctional Chelate-Epoxy Supports," Biotechnology and Bioengineering, vol. 76, No. 3, pp. 269 to 276, (2001).
Haruyama, T., et al., "Protein layer coating method on metal surface by electrochemical process through genetical introduced tag," Biomaterials, vol. 26, No. 24, pp. 4944 to 4947, (2005).
International Search Report Issued Jun. 14, 2011 in PCT/JP11/056871 Filed Mar. 23, 2011.
Extended European Search Report issued on Nov. 6, 2013 in European Patent Application No. 11759404.4.
Cheng Chen, et al., "Immobilized protein ZZ, an affinity tool for immunoglobulin isolation and immunological experimentation", Biotechnology and Applied Biochemistry, vol. 45, No. 2, XP-055085645, Sep. 1, 2006, pp. 87-92.

* cited by examiner

*Primary Examiner* — Daniel E Kolker
*Assistant Examiner* — James Rogers
(74) *Attorney, Agent, or Firm* — Oblon, McClelland, Maier & Neustadt, L.L.P.

(57) ABSTRACT

Provided are a filler for affinity chromatography which has excellent alkali resistance, and a method for isolating immunoglobulin. The filler for affinity chromatography is a filler in which a protein represented by the following formula (1) is immobilized on a carrier.

$$R-R^2 \tag{1}$$

wherein R represents an amino acid sequence consisting of 4 to 300 amino acid residues containing a region consisting of 4 to 20 contiguous histidine residues; and $R^2$ represents an amino acid sequence capable of binding to immunoglobulin, the amino acid sequence consisting of 50 to 500 amino acid residues containing Z domain of Protein A or a fragment thereof, or a variant thereof, provided that the R binds to C-terminus or N-terminus of the $R^2$.

7 Claims, 3 Drawing Sheets

Number of amino acid residues: 258
Mass: 30181.358 (av.) 30163.051(mono.)

MKHHHHHHPMSDYDIPTT<u>ENLYFQG</u>AMVVDNKFNKEQQN

AFYEILHLPNLNEEQRNAFIQSLKDDPSQSANLLAEAKKL

NDAQKEFVDNKFNKEQQNAFYEILHLPNLNEEQRNAFIQS

LKDDPSQSANLLAEAKKLNDAQKELVDNKFNKEQQNAFY

EILHLPNLNEEQRNAFIQSLKDDPSQSANLLAEAKKLNDA

QKKLVDNKFNKEQQNAFYEILHLPNLNEEQRNAFIQSLK

DDPSQSANLLAEAKKLNDAQK

FILLER FOR AFFINITY CHROMATOGRAPHY AND METHOD FOR ISOLATING IMMUNOGLOBULIN

CROSS REFERENCE TO RELATED APPLICATION

This application is a National Stage entry under 35 USC 371 of PCT/JP11/056871, filed on Mar. 3, 2011, and claims priority to Japanese Patent Application No. 2010-068794, filed on Mar. 24, 2010.

FIELD OF THE INVENTION

The present invention relates to a filler for affinity chromatography, and a method for isolating immunoglobulin. Particularly, the present invention relates to a filler for affinity chromatography to which a particular ligand useful for purification of immunoglobulin is bound, and a method for isolating immunoglobulin.

BACKGROUND OF THE INVENTION

Affinity chromatography is chromatography using a column filled with a ligand-immobilized carrier obtained by immobilizing a substance that specifically binds to a substance intended to be separated and purified (ligand), on an insoluble carrier. Affinity chromatography is used for, for example, separation and purification of biological substances such as proteins and nucleic acids (JP-A-H06-281638).

As the carrier for the filler for affinity chromatography, for example, particles obtained by crosslinking sugar chains (represented by agarose gel), or particles containing a synthetic polymer as a main component are used.

However, for use in bioseparation, a filler is usually used repeatedly. However, since there would be residual trace amounts of foreign materials in the filler even after purification operation, usually an operation known as cleaning in place (CIP) is carried out. In the CIP, a reagent capable of eluting foreign substances from the filler (CIP agent) is used. Examples of such reagents include alkaline liquids such as sodium hydroxide. In the case of using sodium hydroxide, foreign substances such as microorganisms, proteins, lipids and nucleic acids can be effectively removed.

PRIOR ART DOCUMENTS

Patent Document

Patent Document 1: JP-A-H06-281638

SUMMARY OF THE INVENTION

Problem to be Solved by the Invention

However, when foreign substances are removed from the filler by using an alkaline liquid, the filler is exposed to an alkaline condition. For a filler for affinity chromatography using a protein as a ligand, such an alkaline condition is severe and may cause a decrease of binding capacity due to decreasing stability of the ligand.

An object of the present invention is to provide a filler for affinity chromatography showing excellent alkali resistance, and a method for isolating immunoglobulin.

Means for Solving the Problem

An aspect of the present invention is a filler for affinity chromatography, wherein a protein ligand represented by the following formula (1) is immobilized on a carrier:

$$R-R^2 \quad (1)$$

wherein R represents an amino acid sequence consisting of 4 to 300 amino acid residues containing a region of 4 to 20 contiguous histidine residues (also referred to as "histidine linker"); and $R^2$ represents an amino acid sequence capable of binding to immunoglobulin, the amino acid sequence consisting of 50 to 500 amino acid residues containing Z domain of Protein A (hereinafter, simply referred to as "Z domain") or a fragment thereof (Z fragment), or a variant thereof (provided that the terminus through which $R^2$ binds to R is C-terminus or N-terminus of immunoglobulin-binding domain of Protein A).

Protein A as used in the present specification is Protein A which is a cell wall component of Staphylococcus aureus.

In the filler for affinity chromatography described above, the amino group in the protein ligand represented by the formula (1) may be immobilized by epoxy group ring-opening reaction with the carrier having epoxy group.

In this case, the carrier may contain substituted 2,3-dihydroxypropyl group as ring-opened epoxy group.

Another aspect of the present invention is a method for isolating immunoglobulin, the method includes:
a step of using said filler for affinity chromatography and adsorbing immunoglobulin to the filler;
a step of eluting the immunoglobulin; and
a step of washing the filler with an alkaline liquid.

According to the present invention, the term "protein" means all molecules which have a peptide structural unit, and represents a concept including, for example, partial fragments of naturally occurring proteins, and variants obtained by artificially modifying the amino acid sequences of naturally occurring proteins. Furthermore, the "immunoglobulin-binding domain" means a functional unit of a polypeptide showing an immunoglobulin-binding activity by itself, and the "immunoglobulin-binding protein" means a protein which shows specific affinity to an immunoglobulin and includes the "immunoglobulin-binding domain." The term "immunoglobulin binding" means binding to a region other than the complementarity determining region (CDR) of an immunoglobulin molecule, particularly the Fc fragment.

According to the present invention, the term "ligand" as used in relation to affinity chromatography means a molecule which binds to target substance in affinity chromatography. A "protein ligand" means a ligand in which the part that binds to the target substance is composed of a protein.

Effects of the Invention

The filler for affinity chromatography shows excellent alkali resistance, and therefore shows high resistance to washing under alkaline condition. Furthermore, when the filler for affinity chromatography is used for, for example, purification of immunoglobulin, since the dynamic binding capacity for immunoglobulin is not easily decreased even if the filler is repeatedly used, the purification of immunoglobulin can be carried out at low cost.

BRIEF DESCRIPTION OF DRAWINGS

FIG. 1 is a diagram illustrating an amino acid sequence of an immunoglobulin-binding protein (SP4Z) (SEQ ID NO:2) prepared in Synthesis Example 2 of the present invention;

DETAILED DESCRIPTION OF THE INVENTION

Figure 2:
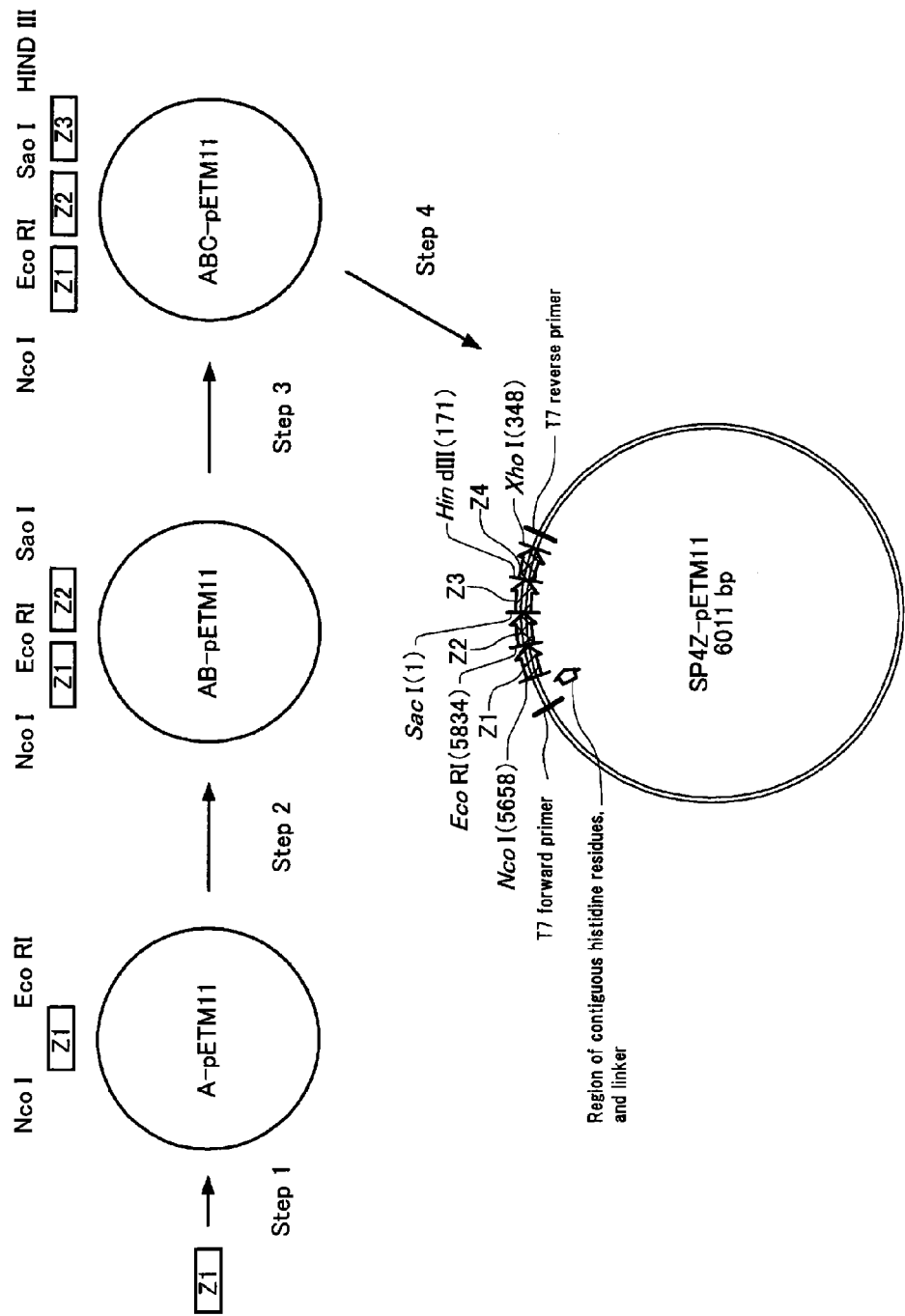
FIG. 2 is a diagram explaining a constitution of a DNA fragment that encodes the immunoglobulin-binding protein according to Synthesis Example 2 of the present invention, which fragment has been inserted into an expression vector (pETM-11)

The filler for affinity chromatography according to an embodiment of the present invention is characterized in that a protein ligand represented by the following formula (1) is immobilized on a carrier:

wherein R represents an amino acid sequence (histidine linker) consisting of 4 to 300 amino acid residues containing a region of 4 to 20 contiguous histidine residues; and $R^2$ represents an amino acid sequence capable of binding to immunoglobulin, the amino acid sequence consisting of 50 to 500 amino acid residues containing Z domain of Protein A (Z domain; SEQ ID NO: 1) or a fragment thereof (Z fragment), or a variant thereof, provided that the R binds to C-terminus or N-terminus of the $R^2$.

1. Filler for Affinity Chromatography 1.1 Carrier 1.1.1 Constitution

The shape of the carrier is not particularly limited, and the carrier may adopt any shape such as a particulate form including an approximate spherical shape or a powder, a fibrous form including a hollow fiber, or a film form. From the viewpoint of increasing surface area and enabling convenient production, a particulate form is preferred. Such particles may be porous or non-porous. A particulate carrier can be used as a packed bed, or can be used in a suspension form. Suspension forms include a fluidized bed (expanded bed) and a product known as a sheer suspension, and particles can freely be moved about therein. In the case of a monolith, a packed bed and a fluidized bed, the order of separation steps generally complies to conventional chromatographic methods based on concentration gradients. In the case of the sheer suspension, a batch method is used. Alternatively, the carrier may be in the form of a chip, a capillary or a filter.

The carrier constituting the filler for affinity chromatography according to the present embodiment has a particle size (mean volume diameter) of preferably 20 μm to 80 μm, and more preferably 30 μm to 60 μm. When the particle size is 20 μm or greater, the column pressure is difficult to be easily increased at a high flow rate. When the particle size is 80 μm or less, the binding capacities of biological substances such as protein ligands and antibodies do not easily decrease. Meanwhile, the "particle size" according to the present invention is the mean volume diameter of the carrier measured by a laser diffraction scattering type particle size distribution analyzer.

The carrier constituting the filler for affinity chromatography according to the present embodiment is preferably porous, and has a specific surface area of 50 m²/g to 150 m²/g, and more preferably 80 m²/g to 120 m²/g. Here, when the specific surface area is 50 m²/g or greater, the binding capacities of biological substances such as protein ligands and antibodies do not easily decrease. On the other hand, when the specific surface area is 150 m²/g or less, the strength of the filler is superior so that the filler is difficult to be easily broken at a high flow rate, and as a result, an increase of pressure inside the column is suppressed. The "specific surface area" according to the present invention is the value obtained by dividing the surface area of a carrier having fine pores having a pore size of 10 nm to 5,000 nm as determined by using a mercury porosimeter, by the dry weight of the carrier.

The carrier that constitutes the filler for affinity chromatography according to the present embodiment has a volume average pore size of preferably 100 nm to 400 nm, and more preferably 200 nm to 300 nm. Here, when the volume average pore size is 100 nm or greater, decrease of the binding capacity at a high flow rate is prevented. On the other hand, when the volume average pore size is 400 nm or less, decrease of the binding capacity is prevented, irrespective of the flow rate. The "volume average pore size" according to the present invention is the volume average pore size of fine pores having a pore size of 10 nm to 5,000 nm as determined by using a mercury porosimeter.

When the particle size, specific surface area and pore size distribution in the ranges described above are satisfied, the balance between a gap between the carriers, which serve as flow channels of the solution to be purified, the pore size in the carrier, and the surface area for binding to the molecules to be purified is optimized, and the binding capacity at a high flow rate is maintained at a high level.

The material of the carrier is, for example, a polymer having a hydrophilic surface, and for example, a polymer having a hydroxyl group (—OH), a carboxyl group (—COOH), an aminocarbonyl group (—CONH₂ or N-substituted type), an amino group (—NH₂ or N-substituted type), an epoxy group, an oligo group or a polyethyleneoxy group at the outer surface (and if available, also at the inner surface). The polymer according to an embodiment is a synthetic polymer such as poly(meth)acrylate, poly(meth)acrylamide, or a styrene-divinylbenzene copolymer. Such a synthetic polymer can be easily produced by a known method such as a method described in, for example, J. MATER. CHEM., 1991, 1(3), 371-374. Alternatively, commercially available products such as TOYOPEARL (Tosoh Corp.) may also be used. The polymer according to another embodiment is a polysaccharide such as dextran, starch, cellulose, pullulan, or agarose. Such polysaccharides are easily produced by known methods, and for example, reference may be made to the method described in Japanese Patent No. 4081143. Alternatively, commercially available products such as SEPHAROSE (GE Healthcare Bioscience Corp.) may also be used. In other embodiments, an inorganic carrier of silica, zirconium oxide or the like may also be used.

One specific example of porous particles used as the carrier in the filler for affinity chromatography according to the present embodiment is, for example, porous organic polymer particles which contains a copolymer of 20% to 50% by weight of a crosslinkable vinyl monomer, 3% to 80% by weight of an epoxy group-containing vinyl monomer, and 20% to 80% by weight of a diol group-containing vinyl monomer (provided that the total amount of the respective monomers is adjusted to 100% by weight), and which has a particle size of 20 μm to 80 μm, a specific surface area of 50 m²/g to 150 m²/g, and a volume average pore size of 100 nm to 400 nm.

Meanwhile, the intrusion volume (pore volume) of fine pores having a pore size of 10 nm to 5,000 nm, in the case where the carrier constituting the filler for affinity chromatography according to the present embodiment is measured with a mercury porosimeter, is preferably 1.3 mL/g to 2.5 mL/g.

1.1.2. Binding to Ligand

As the method for binding between a carrier and a protein ligand, the binding can be generally carried out by using a method of immobilizing the protein on the carrier. Examples include a method of using a carrier having a carboxyl group, and activating this carboxyl group with N-hydroxysuccinic acid imide to react with an amino group of a protein ligand; a method of using a carrier having an amino group or a carboxyl group, and subjecting the carrier to react with a carboxyl group or an amino group of a protein ligand in the presence of a dehydration condensing agent such as a water-soluble carbodiimide, to thereby form an amide bond; a method of using a carrier having a hydroxyl group, and activating the carrier with a cyan halide such as cyan bromide to react with an amino group of a protein ligand; a method of tosylating or tresylating a hydroxyl group of a carrier, and subjecting the carrier to react with an amino group of a protein ligand; a method of introducing an epoxy group to a carrier by means of bisepoxide, epichlorohydrin or the like, and subjecting the carrier to react with an amino group, a hydroxyl group or a thiol group of a protein ligand; and a method of using a carrier having an epoxy group, and subjecting the carrier to react with an amino group, a hydroxyl group or a thiol group of a protein ligand.

The protein ligand used in the present invention is represented by formula (1) that will be described below, and it is preferable to use a method of binding the protein ligand to a carrier by binding to an epoxy group carried by the carrier via an amino group in this protein ligand.

Preferably, the carrier to which the ligand binds may contain substituted 2,3-dihydroxypropyl group as ring-opened epoxy group. This ring-opened epoxy group can be obtained by binding the carrier to the ligand, and then opening the remaining epoxy groups. Preferably, substantially all of the epoxy groups on the carrier are ring-opened before using the filler of the present invention containing the carrier.

The alcoholic hydroxyl group, which is a ring-opened epoxy group produced when an epoxy group is ring-opened, plays roles of hydrophilizing the carrier surface, preventing non-specific adsorption of, for example, proteins, and also enhancing toughness of the carrier in water to thereby preventing destruction of the carrier at a high flow rate. As the method for opening the epoxy ring in a carrier, for example, a method of stirring the carrier in water solvent with an acid or an alkali, under heating or at room temperature, may be used. Furthermore, epoxy groups may also be ring-opened by using a blocking agent having a mercapto group such as mercaptoethanol or thioglycerol, or a blocking agent having an amino group such as monoethanolamine. The most preferred ring-opened epoxy group is a ring-opened epoxy group obtainable by ring-opening an epoxy group contained in a porous carrier by using thioglycerol. Thioglycerol is advantageous in that, the compound has lower toxicity than, for example, mercaptoethanol as a raw material, the epoxy ring-opened group to which the thioglycerol is added exhibits lower non-specific adsorption than a ring-opened group obtained by using a blocking agent having an amino group, and the amount of dynamic binding is large.

If necessary, a molecule (spacer) having an arbitrary length may be introduced between the carrier and the ligand. Examples of the spacer include a polymethylene chain, a polyethylene glycol chain, and saccharides.

1.2. Ligand
1.2.1. Immunoglobulin-Binding Protein

The protein ligand used in the filler for affinity chromatography of the present invention may be an immunoglobulin-binding protein represented by the formula (1) described above. This immunoglobulin-binding protein (hereinafter, also referred to as "protein 1") can be bound to a carrier by, for example, subjecting the protein to react with an epoxy group of the carrier.

In the formula (1), the amino acid sequence represented by R is an amino acid sequence consisting of 4 to 300 amino acid residues containing a region of 4 to 20 contiguous histidine residues. The number of amino acid residues included in R is preferably 8 to 100, and the number of histidine residues in the region of contiguous histidine residues included in R is preferably 4 to 8. Furthermore, in the formula (1), $R^2$ is an amino acid sequence capable of binding to immunoglobulin, the amino acid sequence is consisting of 50 to 500 amino acid residues and containing Z domain of Protein A (SEQ ID NO:1) or a fragment thereof, or a variant thereof. The number of amino acid residues included in the amino acid sequence represented by the $R^2$ is preferably 120 to 480.

In the formula (1) described above, at least one of the amino acid sequence represented by R and the amino acid sequence represented by $R^2$ may contain a domain t which consisting of 1 to 50 amino acids including one kind of amino acid selected from lysine, arginine and cysteine. In this case, plural domain t, which may be identical or different from each other, may be included in the amino acid sequence.

Furthermore, in the formula (1), R— is preferably a group represented by the following formula (2).

$$R^1\text{-r-} \qquad (2)$$

wherein $R^1$ represents an amino acid sequence consisting of 4 to 100 amino acid residues containing a region of 4 to 20 contiguous histidine residues (in $R^1$, the terminus of the region of contiguous histidine residues binds to r); and r represents an optional amino acid sequence consisting of 7 to 200 amino acid residues.

In the formula (2), the number of amino acid residues contained in the amino acid sequence represented by $R^1$ is preferably 4 to 25, the number of histidine residues in the region of contiguous histidine residues contained in $R^1$ is preferably 4 to 8, and the number of amino acid residues contained in the amino acid sequence represented by r is preferably 10 to 50.

Furthermore, the amino acid sequence represented by r shown by the formula (2) may also contain a TEV cleavage site. The "TEV cleavage site according to the present invention refers to an amino acid sequence that can be recognized as a specific cleavage site by a TEV (Tobacco Etch Virus) protease, however, it is not necessary that the TEV cleavage site can be actually cleavable by a TEV protease. Furthermore, the amino acid sequence represented by r may also contain a variant of the TEV domain (at least 70%, and preferably at least 90%, homology with the amino acid sequence of the TEV cleavage site, irrespective of whether the variant can be cleaved by the TEV protease or not).

The total number of amino acid residues constituting the protein 1 is 54 to 800, and in the case of binding the protein 1 to the carrier, the total number is preferably 80 to 600.

1.2.1.1. Immunoglobulin-Binding Domain

In the formula (1), $R^2$ represents an amino acid sequence containing an immunoglobulin-binding domain. The amino acid sequence contains at least one amino acid sequence selected from Z domain of Protein A (Z domain), a fragment thereof (Z fragment), and a variant of the domain or the fragment. The Z domain is described in Nilsson B., et al., Protein Engineering, 1987, Vol. 1, No. 2, p. 107-113). The Z domain has the amino acid sequence represented by SEQ ID NO: 1.

The Z fragment is a fragment of the amino acid sequence of the Z domain, and for example, a fragment having 90% or more of the amino acid sequence of the Z domain is preferred, while a fragment having 95% or more is more preferred. Furthermore, a variant of the Z domain is a variant having at least 90%, preferably at least 95% homology with the amino acid sequence of the Z domain. The variant of the Z domain is preferably a variant showing improved alkali resistance as compared with the Z domain. In this case, whether a variant of the Z domain has improved alkali resistance as compared with the Z domain, can be confirmed by the method described in Examples presented below.

The variant of the Z domain may be, for example, a protein having the sequence described in Japanese Patent No. 4391830. For example, claim 1 of the Japanese Patent No. 4391830 discloses a protein containing two or more of a repeating unit defined by SEQ ID NO:1 (Z domain), in which the amino acid residue at the 23-position is threonine.

Furthermore, in the present invention, $R^2$ may contain the Z domain, a fragment thereof (Z fragment), and variants of the domain and the fragment, singly or in combination of two or more (preferably, 4 to 10).

Preferably, $R^2$ consists of at least one, or a combination of two or more, or 4 to 10 sequences, selected from the Z domain, a Z fragment, and variants thereof.

1.2.1.2. Production of Protein 1

As a standard technology for producing the protein 1, for example, known gene recombination technologies that are described in Frederick M. Ausbel, et al., Current Protocols in Molecular Biology; and Sambrook, et al., ed., Molecular Cloning (Cold Spring Harbor Laboratory Press, $3^{rd}$ Edition, 2001), can be utilized. Specifically, an expression vector containing a nucleic acid sequence encoding a desired modified protein (protein 1) is used for transformation of a host cell such as *Escherichia coli*, and the host cell is cultured in an appropriate liquid medium, to obtain the protein 1 in a large amount and economically from the host cell after culturing. As a preferred expression vector, anyone of known vectors being capable of reproduction in bacteria can be used, and examples thereof include the plasmids described in U.S. Pat. No. 5,151,350, and the plasmids described in Sambrook, et al., ed., Molecular Cloning (Cold Spring Harbor Laboratory Press, $3^{rd}$ edition, 2001). Furthermore, method that is known in the art, for example, Sambrook, et al., ed., Molecular Cloning (Cold Spring Harbor Laboratory Press, $3^{rd}$ edition, 2001) may be used for transformation of a host by introducing a nucleic acid into the host. The method of culturing the transformed bacteria and isolating an expressed protein is well known to ordinary person skilled in the art, and is also illustrated in the Examples of the present invention.

Specifically, the nucleic acid according to another embodiment of the present invention encodes an immunoglobulin-binding protein or a functional variant thereof. According to the present invention, the "functional variant" of an immunoglobulin-binding protein is an immunoglobulin-binding protein modified by, for example, partial addition, deletion or substitution of amino acids, chemical modification of amino acid residues, and means a variant which retains at least 70%, and preferably at least 90%, homology with the amino acid sequence of the immunoglobulin-binding protein before modification, and which can be used as a protein equivalent to the immunoglobulin-binding protein before modification in terms of the immunoglobulin-binding activity. That is, the nucleic acid described above encompasses nucleic acids encoding the protein 1 according to the present specification.

Furthermore, as discussed above, the protein 1 may be a protein containing one or more (preferably 2 to 12, and more preferably 4 to 10) immunoglobulin-binding domains. An appropriate expression plasmid that encodes such a protein can be produced by a method such as described in the Examples of the present invention, and thus, a protein containing one or more immunoglobulin-binding domains can be easily produced.

For example, a protein having the amino acid sequence of SEQ ID NO: 2 (SP4Z) described in the Examples presented below, or a protein having an amino acid sequence obtained by deletion, substitution or addition of one or several amino acid residues in the SEQ ID NO: 2, and having an immunoglobulin-binding activity, is suitable as the immunoglobulin-binding protein used in the present invention.

1.2.1.3. Function and Effect

The filler according to the present embodiment shows high tolerance against washing under alkaline conditions (for example, washing using an alkaline liquid, such as sodium hydroxide solution at 0.01 M to 0.2 M). Although the reason is not clearly known, it can be contemplated that when a region of contiguous histidine residues is added to the Z domain, the position of binding between the carrier and the Z domain is different from the same in the case where a region of contiguous histidine residues is absent, and that a certain structural change occurs in the Z domain after immobilization, leading to an increase of alkali resistance.

1.3. Method for Isolating Immunoglobulin

The method for isolating immunoglobulin according to an embodiment of the present invention is described hereafter. The method for isolating immunoglobulin according to the present embodiment includes a step of using the filler for affinity chromatography of the present invention to adsorb immunoglobulin to the filler (first step); a step of eluting the immunoglobulin (second step); and a step of washing the filler with an alkaline liquid (third step).

In the first step, a solution containing immunoglobulin is applied to, for example, a column filled with the filler for affinity chromatography, under the conditions where the immunoglobulin adsorbs to the protein ligand of the filler. The solution containing immunoglobulin may be a solution containing immunoglobulin, and examples include a biological sample such as blood serum, and a supernatant of a hybridoma medium. The conditions where the immunoglobulin adsorbs may be a condition where, for example, immunoglobulin concentration of 0.1 g/L to 10 g/L, pH of solution of 5 to 9, retention time in the column of 0.5 minutes to 50 minutes, and a temperature of 0° C. to 40° C.

In this first step, most of substances other than immunoglobulin in the solution pass through the column without being adsorbed. Usually, in order to remove some substances that are weakly retained, the filler is washed with a neutral buffer solution containing a salt such as NaCl, for example, a sodium dihydrogen phosphate/disodium hydrogen phosphate solution, a citric acid/disodium hydrogen phosphate solution, a hydrochloric acid/tris(hydroxymethyl)aminomethane solution, or a HEPES/sodium hydroxide solution. In the second step, the immunoglobulin is eluted by applying an appropriate buffer solution at pH 2 to 5, for example, a citric acid/sodium citrate solution, an acetic acid/sodium acetate solution, or a hydrochloric acid/glycine solution. In the third step, the filler is washed with an alkaline liquid (CIP washing).

Examples of the alkaline liquid used in the method for isolating immunoglobulin according to the present embodiment, include an aqueous sodium hydroxide solution, an aqueous potassium hydroxide solution, triethylamine, and tetrabutylammonium hydroxide.

EXAMPLES

2. Examples

Hereinafter, the filler for affinity chromatography according to the present embodiment is more specifically explained by way of Examples. Furthermore, the following descriptions only illustrate the embodiments of the present invention, and the scope of the present invention is not limited to such descriptions.

2.1. Synthesis Example 1

Synthesis of Porous Particles 8.2 g of glycidyl methacrylate (manufactured by Mitsubishi Rayon Co., Ltd.), 65.9 g of trimethylolpropane trimethacrylate (manufactured by Sartomer Company, Inc.), and 90.6 g of glycerin monomethacrylate (manufactured by NOF Corp.) were dissolved in 245.8 g of 2-octanone (manufactured by Toyo Gosei Co., Ltd.) and 62 g of acetophenone (manufactured by Wako Pure Chemical Industries, Ltd.), and 2 g of 2,2'-azoisobutyronitrile (manufactured by Wako Pure Chemical Industries, Ltd.) was added thereto. Thus, an organic monomer solution was prepared.

Subsequently, 8.5 g of polyvinyl alcohol (PVA-217 manufactured by Kuraray Co., Ltd.), 0.43 g of sodium dodecyl sulfate (EMAL 10G manufactured by Kao Corp.), and 21.3 g of sodium sulfate (manufactured by Wako Pure Chemical Industries, Ltd.) were added to 4240 g of pure water, and the mixture was stirred overnight, to prepare an aqueous solution.

Next, the aqueous solution thus obtained was introduced into a 7-L separable flask equipped with a thermometer, a stirring blade and a cooling tube, and was placed in a warm water bath. Stirring was started at 600 rpm in a nitrogen atmosphere. Subsequently, the separable flask was warmed by a warm water bath, and when the temperature of the aqueous solution reached 85° C., the organic monomer solution was added to this aqueous solution by using a dropping funnel. The mixture was stirred for 5 hours.

Subsequently, the reaction liquid was cooled, and then transferred into a 5-L bin made of polypropylene. The reaction liquid was left to stand until the particles floated, and excess water was discarded by suctioning the lower layer. Furthermore, acetone was added to this reaction liquid, and thereby particles were precipitated. Subsequently, the reaction liquid was left to stand for 3 minutes, and acetone was removed by decantation. This operation was repeated twice, and then particles were precipitated by adding water to the reaction liquid. Furthermore, the reaction liquid was left to stand for 3 minutes, and decantation was performed. This operation was repeated twice, and thereby the particles were washed. Furthermore, a dispersion liquid of the particles was replaced with acetone again, and the particles were air dried overnight and then dried in a vacuum dryer. Thus, 90 g of porous particles (hereinafter, indicated as PB) were obtained. The average particle size of PB was 43 μm, and the specific surface area was 83 $m^2/g$.

2.2. Synthesis Example 2

Production of Protein Ligand 2.2.1. Production of Immunoglobulin-Binding Protein 2.2.1.1. Construction of a Vector Expressing Immunoglobulin-Binding Protein An expression vector for immunoglobulin-binding protein (SP4Z) was constructed by the following steps (i) to (iv). FIG. 2 is a diagram explaining the method for constructing an SP4Z vector (SP4Z-pETM11).

(i) Step 1

A monomer Z domain vector (A-pETM11) having an NcoI cleavage site and an EcoRI cleavage site was constructed by using a DNA encoding a monomer Z domain as a starting material.

2.2.1.2. Construction of SP1Z-pETM11 Vector (Vector for Monomer Z Domain having Stop Codon)

PCR was carried out by using SPZK DNA (SEQ ID NO:3) as a template, and using Primer 153 (SEQ ID NO:5) as a forward primer and Primer 156 (SEQ ID NO:8) as a reverse primer. Primer 153 and Primer 156 contain an NcoI cleavage site and a SacI restriction enzyme cleavage site, respectively. The conditions for PCR are as follows.

Stage 1: One cycle, for 1 minute at 94° C.; stage 2: for 30 seconds at 94° C., for 30 seconds at 55° C., and for 2.5 minutes at 72° C. (25 cycles); stage 3: one cycle, for 10 minutes at 72° C., and then the reaction system was maintained at 4° C.

The PCR product was purified with a PCR purification kit (Illustra GFX-96 PCR Purification Kit; manufactured by GE Healthcare Bioscience Corp.), and electrophoresis was carried out at 100 V for 45 minutes by using a 1% agarose TAE gel. Bands thus obtained were purified with a gel extraction kit (Illustra GFX PCR DNA Band Purification Kit; manufactured by GE Healthcare Bioscience Corp.). Subsequently, ligation of a pETM11 vector (European Molecular Biology Laboratory) cleaved by using NcoI restriction enzyme and SacI restriction enzyme, and the PCR product was carried out. The digestion reactions based on restriction enzymes were carried out for one hour at 37° C. by using NcoI restriction enzyme and SacI restriction enzyme, both manufactured by New England Biolabs, Inc., and the reaction product was purified by electrophoresis and then purified by using a gel extraction kit.

The ligation reaction was carried out overnight at room temperature by using T4 DNA ligase (manufactured by Invitrogen, Inc.).

The vector obtained by ligation was used to transform DH5α competent cell (manufactured by Biomedal Life Science S.L.), and the transformant thus obtained was cultured overnight in LB medium containing kanamycin at 37° C. The plasmid was extracted from a portion of the medium, and the sequence of the inserted DNA fragment was confirmed by using a DNA sequencer (3730 DNA Sequencer; manufactured by Applied Biosystems, Inc.).

2.2.1.3. Construction of A-pETM11 Vector (Monomer Z Domain Vector without Stop Codon)

A-pETM11 vector was constructed in the same manner as in Experiment 2.2.1.2., by using Primer 153 as a forward primer and Primer 154 (SEQ ID NO: 6) as a reverse primer, instead of Primers 153 and 156. Meanwhile, the insertion of the DNA fragment was carried out by utilizing the NcoI cleavage site and the EcoRI cleavage site of pETM11.

(ii) Step 2

Next, one more Z domain was added to the A-pETM11 vector, and thus a vector for dimer Z domain (AB-pETM11) having an EcoRI cleavage site and a SacI cleavage site was constructed.

2.2.1.4. Construction of SP2Z-pETM11 Vector (Vector for Dimer Z Domain having Stop Codon)

The DNA of monomer Z domain having an EcoRI cleavage site and a SacI cleavage site was prepared by PCR by using SPZK DNA (SEQ ID NO:3) as a template, and using Primer 155 (SEQ ID NO:7) as a forward primer and Primer 156 as a reverse primer, and the DNA was inserted into the EcoRI cleavage site and the SacI cleavage site of A-pETM11. The experiment was carried out under the same conditions as in Experiment 2.2.1.2.

2.2.1.5. Construction of AB-pETM11 Vector (Vector for Dimer Z Domain without Stop codon)

The DNA of monomer Z domain having an EcoRI cleavage site and a SadI cleavage site, without any stop codon, was prepared by PCR by using SPZK DNA (SEQ ID NO:3) as a template, and using Primer 155 as a forward primer and Primer 157 (SEQ ID NO:9) as a reverse primer, and the DNA was inserted into the EcoRI cleavage site and the SadI cleavage site of A-pETM11. Thus, AB-pETM11 vector was constructed. The experiment was carried out under the same conditions as in Experiment 2.2.1.2.

(iii) Step 3

Next, one Z domain was further added to the AB-pETM11 vector, and thus a vector for trimer Z domain (ABC-pETM11) having a SadI cleavage site and a HindIII cleavage site, was constructed.

2.2.1.6. Construction of SP3Z-pETM11 vector (vector for trimer Z domain having stop codon)

The DNA of monomer Z domain having a SacI cleavage site and a XhoI cleavage site was prepared by PCR by using SPZK DNA (SEQ ID NO:3) as a template and by using Primer 158 (SEQ ID NO:10) as a forward primer and Primer 161 (SEQ ID NO: 13) as a reverse primer, and the DNA was inserted into the EcoRI cleavage site and the SadI cleavage site of AB-pETM11. The experiment was carried out under the same conditions as in Experiment 2.2.1.2.

2.2.1.7. Construction of ABC-pETM11 Vector (Vector for Trimer Z Domain without Stop Codon)

The DNA of monomer Z domain having a SacI cleavage site and a HindIII cleavage site, without any stop codon, was prepared by PCR by using SPZK DNA (SEQ ID NO:3) as a template and by using Primer 158 as a forward primer and Primer 159 (SEQ ID NO:11) as a reverse primer, and the DNA was inserted into the SadI cleavage site and the HindIII cleavage site of AB-pETM11. Thus, an ABC-pETM11 vector was constructed. The experiment was carried out under the same conditions as in Experiment 2.2.1.2.

(iv) Step 4

Finally, a fourth Z domain was added to the ABC-pETM11 vector, and thus a SP4Z-pETM11 vector having a HindIII cleavage site and a XhoI cleavage site was constructed.

2.2.1.8. Construction of SP4Z-pETM11 Vector (Vector for Tetramer Z Domain having Stop Codon)

The DNA of monomer Z domain having a HindIII cleavage site and a XhoI cleavage site was prepared by PCR by using SPZK DNA (SEQ ID NO:3) as a template and using Primer 160 (SEQ ID NO:12) and Primer 161, and the DNA was inserted into the HindIII cleavage site and the XhoI cleavage site of ABC-pETM11. Thus, a SP4Z-pETM11 vector was constructed. The experiment was carried out under the same conditions as in Experiment 2.2.1.2.

2.2.1.9. Expression and Purification of SP4Z

The SP4Z-pETM11 vector thus obtained was introduced into *E. coli* (strain BL21) cells (manufactured by Stratagene Corp.), 1 mM IPTG (isopropyl-β-thiogalactopyranoside; manufactured by Sigma-Aldrich Company) was added thereto at 18° C., and the cells were incubated for 15 hours. Thus, a recombinant immunoglobulin-binding protein (protein 1) was expressed. Prior to induction, the cells were incubated at 37° C. until the absorbance (OD600) reached about 0.6. After the protein was expressed, the cells were collected and disrupted in a Tris buffer solution at pH 8.0.

The recombinant immunoglobulin-binding protein (SP4Z) thus obtained was purified by Ni affinity chromatography (Ni-NTA (nitrilotriacetic acid) particles, manufactured by Qiagen N.V.). The purified immunoglobulin-binding protein was further purified by anion exchange chromatography (Q-Sepharose FF, manufactured by GE Healthcare Bioscience Corp.). The purity of the immunoglobulin-binding protein measured by SDS gel electrophoresis was 96% by mass.

Furthermore, for the recombinant immunoglobulin-binding protein (SP4Z) thus obtained, the molecular weight was measured by a time of flight mass spectrometry (MALDI-TOF/MS) spectral analysis.

The amino acid sequence of the immunoglobulin-binding protein SP4Z prepared as described above is shown in FIG. 1. In FIG. 1, R and $R^2$ respectively correspond to R and $R^2$ in the formula (1), and $R^1$ and r respectively correspond to $R^1$ and r in the formula (2). The underlined part in r represents the TEV cleavage site. Furthermore, the Z fragment in FIG. 1 has an amino acid sequence obtained by removing the amino acid residues APK from the C-terminus of the Z domain represented by SEQ ID NO: 1.

2.2.2. Production of SP4ZwoHis

To 15 mL of a buffer (pH 8.0) of 50 mM Tris-hydrochloric acid, 0.5 mM EDTA (ethylenediaminetetraacetic acid) and 1 mM DTT (dithiothreitol), 150 mg of SP4Z and 900 U of MobiTEV protease (MoBiTec GmbH) were added, and the mixture was stirred for 12 hours at 30° C. Thus, the TEV cleavage site of SP4Z was cleaved. The SP4Z cleaved with TEV protease was passed through a Ni-NTA column (capacity: 4 mL), and thus crude SP4ZwoHis, in which the histidine linker of SP4Z was cleaved, was collected. The crude SP4ZwoHis thus obtained was further purified by anion exchange chromatography (Q-Sepharose FF, manufactured by GE Healthcare Bioscience Corp.) in a HEPES buffer solution at pH 7.5. This protein 1woHis was concentrated with a centrifugal concentrator (Vivaspin 20, manufactured by Sartorius AG), and then the protein was dialyzed for 12 hours in 10 mM HEPES buffer (pH 7.5). Thus, SP4ZwoHis (SEQ ID NO: 4) was prepared.

2.3. Synthesis Example 3

Immobilization of Immunoglobulin-Binding Protein on Particle 2.3.1. Immobilization Example A liquid mixture in which 1.1 mL of PB and 20 mg of SP4Z are dispersed in 10 mL of a 0.1 M phosphate buffer (pH 6.8) was prepared, and then 2.1 g of sodium sulfate was added thereto. The mixture was mixed by inverting for 24 hours at 25° C., for binding the SP4Z to PB (porous particles of a glycidyl methacrylate-trimethylolpropane trimethacrylate-glylcerin monomethacrylate copolymer). The particles thus produced were filtered, and then were mixed with 10 mL of 5 M thioglycerol. The mixture was subjected to react for 4 hours at 30° C., and remaining epoxy groups were blocked. The particles were washed with PBS/0.05%l Tween 20, and then washed with PBS. Thus, 1.1 mL of SP4Z-bound porous particles (SP4Z-PB) was obtained.

2.3.2. Immobilization Example 2

The process was carried out in the same manner as in Immobilization Example 1, except that SP4ZwoHis was used instead of SP4Z used in Immobilization Example 1. Thus, 1.1 mL of SP4ZwoHis-bound porous particles (SP4ZwoHis-PB) was obtained.

2.3.3. Immobilization Example 3

The process was carried out in the same manner as in Immobilization Example 1, except that Epoxy-activated Sepharose 6B (manufactured by GE Healthcare Bioscience Corp.) was used instead of PB used in Immobilization Example 1. Thus, 1.1 mL of SP4Z-bound agarose particles (protein 1-AG) was obtained.

2.3.4. Immobilization Example 4

The process was carried out in the same manner as in Immobilization Example 1, except that Epoxy-activated Sepharose 6B (manufactured by GE Healthcare Bioscience Corp.) was used instead of PB used in Immobilization Example 1, and SP4ZwoHis was used instead of SP4Z. Thus, 1.1 mL of SP4ZwoHis-bound agarose particles (SP4ZwoHis-AG) was obtained.

2.4. Test Example

2.4.1. Measurement Example 1

Measurement of Dynamic Binding Capacity for Immunoglobulin G (IgG)

SP4Z-PB, SP4ZwoHis-PB, SP4Z-AG, and SP4ZwoHis-AG were each filled in a column having an inner diameter of 0.5 cm up to a bed height of 5 cm. Each of the columns was equilibrated with a 20 mM phosphate buffer (pH 7.4), and then a 20 mM phosphate buffer containing human polyclonal IgG (5 mg/mL) was applied at a linear flow rate of 60 cm/hour. The amount of human polyclonal IgG adsorption obtained when the human polyclonal IgG in the eluent underwent 10% breakthrough (destruction) by absorbance monitoring, was divided by the filler volume, and thereby the dynamic binding capacity per unit volume of the filler was determined. The results are shown in Table 1.

TABLE 1

| Filler | IgG dynamic binding capacity (mg/mL) |
|---|---|
| SP4Z-PB | 37 |
| SP4ZwoHis-PB | 33 |
| SP4Z-AG | 24 |
| SP4ZwoHis-AG | 18 |

2.4.2. Measurement Example 2

Measurement of Alkali Resistance

A column filled with each of the fillers used in Measurement Example 1 was mounted in a low pressure chromatography system (AKTA Prime Plus; manufactured by GE Healthcare Bioscience Corp.), and 10 ml of 0.1 M sodium hydroxide was applied to the column. The column was removed from the apparatus and sealed, and the column was left to stand for a certain time at room temperature. Subsequently, the binding capacity for human polyclonal IgG at a linear flow rate of 60 cm/hour was measured in the same manner as in Measurement Example 1. The binding capacity retention rate was determined relative to the case where the binding amount of human polyclonal IgG before the treatment with 0.1 M sodium hydroxide was designated as 100%. The results are shown in FIG. 3.

Figure 3:
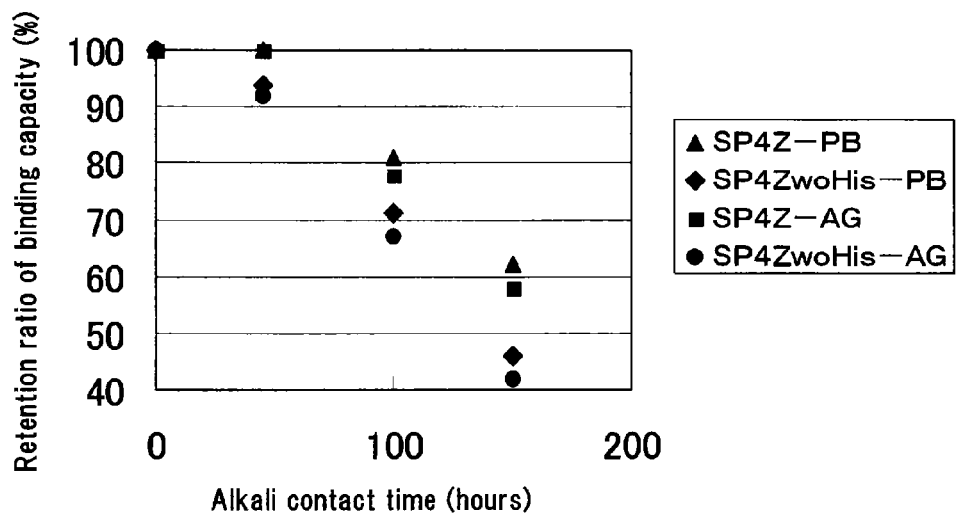
FIG. 3 is a graph illustrating a result of evaluation of alkali resistance in Measurement Example 2 of the present invention.

According to FIG. 3, the fillers (SP4Z-PB and SP4Z-AG), to which an immunoglobulin binding protein (SP4Z) having a histidine linker was bound, exhibited a small decrease in the retention ratio of the binding capacity even if the alkali contact time was increased, as compared with the fillers (SP4ZwoHis-PB and SP4ZwoHis-AG) to which an immunoglobulin binding protein which did not have a histidine linker was bound. Accordingly, it was confirmed that the fillers to which a protein ligand represented by the formula (1) was immobilized, had excellent alkali tolerance.

The present invention is not intended to be limited to the embodiments described above, and various new alterations are possible. Furthermore, the present invention includes constitutions that are substantially identical with the constitutions described in the embodiments (for example, constitutions having identical functions, methods and results, or constitutions having identical purposes and results). Furthermore, the present invention includes constitutions in which the parts that are not essential in the constitutions described in the embodiments have been changed. Further, the present invention includes constitutions which provide the same operating effects, or constitutions which can achieve the same purpose, as the constitutions described in the embodiments. Further, the present invention includes constitutions to which known technologies have been added to the constitutions described in the embodiments.

The invention claimed is:

1. A filler for affinity chromatography, comprising a protein ligand represented by the following formula (1) immobilized on a carrier:

$$R—R^2 \qquad (1),$$

wherein R represents an amino acid sequence having from 4 to 300 amino acid residues comprising a region of from 4 to 20 contiguous histidine residues; and $R^2$ represents an amino acid sequence which binds to immunoglobulin, and has from 50 to 500 amino acid residues comprising a Z domain of Protein A or an amino acid sequence having at least 95% identity to the Z domain of Protein A, wherein the amino acid sequence R binds to a C-terminus or N-terminus of the amino acid sequence $R^2$, wherein the carrier is at least one synthetic polymer selected from the group consisting of poly(meth)acrylate, poly(meth)acrylamide, and a styrene-divinylbenzene copolymer, and wherein the protein ligand is bound to an epoxy group carried by the carrier via an amino group in this protein ligand.

2. The filler for affinity chromatography according to claim 1, wherein the carrier comprises a substituted 2,3-dihydroxypropyl group as a ring-opened epoxy group.

3. The filler according to claim 1, wherein the carrier has a mean volume diameter of from 20 μm to 80 μm.

4. The filler according to claim 1, wherein the carrier is porous and has a specific surface area of from 50 m$^2$/g to 150 m$^2$/g.

5. The filler according to claim 1, wherein the carrier has a volume average pore size of from 100 nm to 400 nm.

6. A filler for affinity chromatography, comprising a protein ligand represented by the following formula (1) immobilized on a carrier:

$$R—R^2 \qquad (1),$$

wherein R represents an amino acid sequence having from 4 to 300 amino acid residues comprising a region of from 4 to 20 contiguous histidine residues; and $R^2$ represents an amino acid sequence which binds to immunoglobulin and has from 50 to 500 amino acid residues comprising an amino acid sequence having at least 95% identity to a Z domain of Protein A, wherein the amino acid sequence R binds to a C-terminus or N-terminus of the amino acid sequence $R^2$, wherein the carrier is at least one synthetic polymer selected from the group consisting of poly(meth)acrylate, poly(meth)acrylamide, and a styrene-divinylbenzene copolymer, and wherein the protein ligand is bound to an epoxy group carried by the carrier via an amino group in this protein ligand.

7. A method for isolating an immunoglobulin, the method comprising:
adsorbing the immunoglobulin to the filler according to claim 1;
eluting the immunoglobulin; and
washing the filler with an alkaline solution.

* * * * *

SEQUENCE LISTING

```
<160> NUMBER OF SEQ ID NOS: 13

<210> SEQ ID NO 1
<211> LENGTH: 58
<212> TYPE: PRT
<213> ORGANISM: Staphylococcus aureus
<220> FEATURE:
<223> OTHER INFORMATION: Z domain

<400> SEQUENCE: 1

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
```

```
                35                  40                  45
Lys Lys Leu Asn Asp Ala Gln Ala Pro Lys
    50                  55
```

<210> SEQ ID NO 2
<211> LENGTH: 258
<212> TYPE: PRT
<213> ORGANISM: Staphylococcus aureus
<220> FEATURE:
<223> OTHER INFORMATION: SP4Z

<400> SEQUENCE: 2

```
Met Lys His His His His His His Pro Met Ser Asp Tyr Asp Ile Pro
1               5                   10                  15

Thr Thr Glu Asn Leu Tyr Phe Gln Gly Ala Met Val Val Asp Asn Lys
            20                  25                  30

Phe Asn Lys Glu Gln Gln Asn Ala Phe Tyr Glu Ile Leu His Leu Pro
        35                  40                  45

Asn Leu Asn Glu Glu Gln Arg Asn Ala Phe Ile Gln Ser Leu Lys Asp
    50                  55                  60

Asp Pro Ser Gln Ser Ala Asn Leu Leu Ala Glu Ala Lys Lys Leu Asn
65                  70                  75                  80

Asp Ala Gln Lys Glu Phe Val Asp Asn Lys Phe Asn Lys Glu Gln Gln
                85                  90                  95

Asn Ala Phe Tyr Glu Ile Leu His Leu Pro Asn Leu Asn Glu Glu Gln
            100                 105                 110

Arg Asn Ala Phe Ile Gln Ser Leu Lys Asp Asp Pro Ser Gln Ser Ala
        115                 120                 125

Asn Leu Leu Ala Glu Ala Lys Lys Leu Asn Asp Ala Gln Lys Glu Leu
    130                 135                 140

Val Asp Asn Lys Phe Asn Lys Glu Gln Gln Asn Ala Phe Tyr Glu Ile
145                 150                 155                 160

Leu His Leu Pro Asn Leu Asn Glu Glu Gln Arg Asn Ala Phe Ile Gln
                165                 170                 175

Ser Leu Lys Asp Asp Pro Ser Gln Ser Ala Asn Leu Leu Ala Glu Ala
            180                 185                 190

Lys Lys Leu Asn Asp Ala Gln Lys Lys Leu Val Asp Asn Lys Phe Asn
        195                 200                 205

Lys Glu Gln Gln Asn Ala Phe Tyr Glu Ile Leu His Leu Pro Asn Leu
    210                 215                 220

Asn Glu Glu Gln Arg Asn Ala Phe Ile Gln Ser Leu Lys Asp Asp Pro
225                 230                 235                 240

Ser Gln Ser Ala Asn Leu Leu Ala Glu Ala Lys Lys Leu Asn Asp Ala
                245                 250                 255

Gln Lys
```

<210> SEQ ID NO 3
<211> LENGTH: 213
<212> TYPE: DNA
<213> ORGANISM: Staphylococcus aureus
<220> FEATURE:
<223> OTHER INFORMATION: SPZK DNA

<400> SEQUENCE: 3

```
atgcatcatc atcatcatca cgtgaattcg ctcgaggtgg ataacaaatt caacaaagaa      60
caacaaaatg ctttctatga aatcttacat ttacctaact taaacgaaga acaacgcaat     120
```

```
gctttcatcc aaagcctaaa agatgaccca agccaaagcg ctaaccttt agcagaagct      180 aaaaagctaa atgatgcaca aggatctaaa taa                                  213
```

<210> SEQ ID NO 4
<211> LENGTH: 291
<212> TYPE: PRT
<213> ORGANISM: Staphylococcus aureus
<220> FEATURE:
<223> OTHER INFORMATION: SPATK

<400> SEQUENCE: 4

```
Met Lys His His His His His His Pro Met Ser Asp Tyr Asp Ile Pro
1               5                   10                  15

Thr Thr Glu Asn Leu Tyr Phe Gln Gly Ala Met Ala Lys Ala Asp Ala
            20                  25                  30

Gln Gln Asn Asn Phe Asn Lys Asp Gln Gln Ser Ala Phe Tyr Glu Ile
        35                  40                  45

Leu Asn Met Pro Asn Leu Asn Glu Ala Gln Arg Asn Gly Phe Ile Gln
    50                  55                  60

Ser Leu Lys Asp Asp Pro Ser Gln Ser Thr Asn Val Leu Gly Glu Ala
65                  70                  75                  80

Lys Lys Leu Asn Glu Ser Gln Ala Pro Lys Ala Asp Asn Asn Phe Asn
                85                  90                  95

Lys Glu Gln Gln Asn Ala Phe Tyr Glu Ile Leu Asn Met Pro Asn Leu
            100                 105                 110

Asn Glu Glu Gln Arg Asn Gly Phe Ile Gln Ser Leu Lys Asp Asp Pro
        115                 120                 125

Ser Gln Ser Ala Asn Leu Leu Ser Glu Ala Lys Lys Leu Asn Glu Ser
    130                 135                 140

Gln Ala Pro Lys Ala Asp Asn Lys Phe Asn Lys Glu Gly Ser Ser Gly
145                 150                 155                 160

Lys Ala Asp Ala Gln Gln Asn Asn Phe Asn Lys Asp Gln Gln Ser Ala
                165                 170                 175

Phe Tyr Glu Ile Leu Asn Met Pro Asn Leu Asn Glu Ala Gln Arg Asn
            180                 185                 190

Gly Phe Ile Gln Ser Leu Lys Asp Asp Pro Ser Gln Ser Thr Asn Val
        195                 200                 205

Leu Gly Glu Ala Lys Lys Leu Asn Glu Ser Gln Ala Pro Lys Ala Asp
    210                 215                 220

Asn Asn Phe Asn Lys Glu Gln Gln Asn Ala Phe Tyr Glu Ile Leu Asn
225                 230                 235                 240

Met Pro Asn Leu Asn Glu Glu Gln Arg Asn Gly Phe Ile Gln Ser Leu
                245                 250                 255

Lys Asp Asp Pro Ser Gln Ser Ala Asn Leu Leu Ser Glu Ala Lys Lys
            260                 265                 270

Leu Asn Glu Ser Gln Ala Pro Lys Ala Asp Asn Lys Phe Asn Lys Glu
        275                 280                 285

Gly Ser Lys
    290
```

<210> SEQ ID NO 5
<211> LENGTH: 38
<212> TYPE: DNA
<213> ORGANISM: Artificial
<220> FEATURE:
<223> OTHER INFORMATION: primer containing NcoI cutting site

```
<400> SEQUENCE: 5
ggaggaccat ggttgtggat aacaaattca acaaagaa                              38

<210> SEQ ID NO 6
<211> LENGTH: 39
<212> TYPE: DNA
<213> ORGANISM: Artificial
<220> FEATURE:
<223> OTHER INFORMATION: primer containing EcoRI cutting site

<400> SEQUENCE: 6
ggtggtgaat tcttttttgtg catcatttag cttttttagc                           39

<210> SEQ ID NO 7
<211> LENGTH: 37
<212> TYPE: DNA
<213> ORGANISM: Artificial
<220> FEATURE:
<223> OTHER INFORMATION: primer containing EcoRI cutting site

<400> SEQUENCE: 7
ggaggagaat tcgtggataa caaattcaac aaagaac                               37

<210> SEQ ID NO 8
<211> LENGTH: 36
<212> TYPE: DNA
<213> ORGANISM: Artificial
<220> FEATURE:
<223> OTHER INFORMATION: primer containing SacI cutting site

<400> SEQUENCE: 8
ggtggtgagc tcctattttt gtgcatcatt tagctt                                36

<210> SEQ ID NO 9
<211> LENGTH: 33
<212> TYPE: DNA
<213> ORGANISM: Artificial
<220> FEATURE:
<223> OTHER INFORMATION: primer containing SacI cutting site

<400> SEQUENCE: 9
ggtggtgagc tcttttttgtg catcatttag ctt                                  33

<210> SEQ ID NO 10
<211> LENGTH: 36
<212> TYPE: DNA
<213> ORGANISM: Artificial
<220> FEATURE:
<223> OTHER INFORMATION: primer containing SacI cutting site

<400> SEQUENCE: 10
ggaggagagc tcgtggataa caaattcaac aaagaa                                36

<210> SEQ ID NO 11
<211> LENGTH: 39
<212> TYPE: DNA
<213> ORGANISM: Artificial
<220> FEATURE:
<223> OTHER INFORMATION: primer containing HindIII cutting site

<400> SEQUENCE: 11
ggtggtaagc tttttttgtg catcatttag cttttttagc                            39

<210> SEQ ID NO 12
<211> LENGTH: 36
```

-continued

```
<212> TYPE: DNA
<213> ORGANISM: Artificial
<220> FEATURE:
<223> OTHER INFORMATION: primer containing HindIII cutting site

<400> SEQUENCE: 12
ggaggaaagc ttgtggataa caaattcaac aaagaa                              36

<210> SEQ ID NO 13
<211> LENGTH: 36
<212> TYPE: DNA
<213> ORGANISM: Artificial
<220> FEATURE:
<223> OTHER INFORMATION: primer containing XhoI cutting site

<400> SEQUENCE: 13
ggtggtctcg agctattttt gtgcatcatt tagctt                              36
```